United States Patent [19]

Newhouse et al.

[11] Patent Number: 4,822,337

[45] Date of Patent: Apr. 18, 1989

[54] INSULIN DELIVERY METHOD AND APPARATUS

[76] Inventors: Stanley Newhouse, 206 Juniper Cir. North, Lawrence, N.Y. 11559; Robert Lerner, 315 E. 65th St., New York, N.Y. 10021; Roy Martin, 3312 182nd Pl., NE., Redmond, Wash. 98452

[21] Appl. No.: 64,355

[22] Filed: Jun. 22, 1987

[51] Int. Cl.⁴ .............................................. A61M 31/00
[52] U.S. Cl. .......................................... 604/50; 604/66
[58] Field of Search ........................ 604/50, 51, 52, 65, 604/66, 67

[56] References Cited

U.S. PATENT DOCUMENTS 4,526,568  7/1985  Clemens et al. ...................... 604/50

FOREIGN PATENT DOCUMENTS 2153081  8/1985  United Kingdom ................. 604/50

Primary Examiner—John D. Yasko
Attorney, Agent, or Firm—Wolder, Gross & Yavner

[57] ABSTRACT

A method and apparatus for providing for the insulin needs of a diabetic individual utilizes blood flow in the digestive tract as the operative variable. Such blood flow is monitored and when deviations from a base level are sensed insulin is provided in measured amounts. The blood flow may be monitored on a continuous basis to provide real-time analysis and delivery. The system may be under microprocessor control, and may include recording means to allow a record of blood flow and insulin delivery to be made either for insulin need computation or for later review.

16 Claims, 3 Drawing Sheets

INSULIN DELIVERY METHOD AND APPARATUS

BACKGROUND

The present invention is directed to an insulin delivery method and apparatus and in particular to a closed-loop system in which the body's requirements for insulin will be delivered as needed by the system on a continuous basis in the amounts required.

The normal functioning of the human body provides for extremely precise maintenance of various constituents of bodily fluids. This consistency is the result of the operation of several physiological mechanisms, including the negative-feedback system of the endocrine system. Physiologic events brought about by changes in the concentration of a given substance result in the restoration of the substance to its original concentration. For example, a rise in the blood sugar level causes an increase in the amount of insulin secreted by the pancreas. The resulting increase in the amount of circulating insulin affects many body tissues in a manner which causes a portion of the sugar to leave the circulating fluids to an extent which results in a restoration of the blood sugar level to its appropriate physiologic range. The decrease in blood sugar inhibits the further release of insulin, halting the removal of blood sugar from the system such that the re-established concentration is maintained.

In the healthy, non-diabetic individual, this closed loop system operates properly, and the blood sugar level varies little, except for a short period after meals when the blood sugar level increases. In the non-diabetic individual this increase is restricted in both magnitude and duration. In the patient with diabetes, however, this control is lost, and accordingly external mechanisms must be employed to control the blood sugar level.

In the past, such systems have been of the open loop variety, and are employed to introduce into the body a predetermined amount of insulin, irrespective of the precise needs of the body at that point in time. The dosage level may be determined by the consideration of a variety of generalized factors, including the age, weight and health of the individual, as well as other pertinent factors, but ultimately is an educated guess as to the patient's actual requirements.

Illustrative of such systems are those of U.S. Pat. No. 4,559,037 of Dec. 17, 1985 to Franetzki; U.S. Pat. No. 4,601,707 of July 22, 1986 to Albisser et al; and U.S. Pat. No. 4,398,908 of Aug. 16, 1983 to Siposs. None of these systems provides a mechanism by which actual insulin needs can be estimated and accordingly cannot provide the "fine tuning" of insulin delivery required for optimum body health.

In addition to the increase in blood sugar which rises after a meal blood circulation to and from the digestive tract similarly rises. Rather than the direct monitoring of blood sugar level, the present invention relies upon the sensing of digestive system blood flow to provide a means of real time sensing required for a closed loop insulin delivery system. As the circulation to and from the digestive system increases with food ingestion and decreases during stress reactions in a manner analogous to bodily insulin release, monitoring of this blood flow provides an acceptable basis around which an insulin delivery system can be designed.

SUMMARY OF THE INVENTION

An object of the present invention is to provide an insulin delivery system of the closed loop variety which allows for real time analysis of the body's insulin needs.

A further object of the present invention is to provide an insulin delivery system which utilizes digestive system blood flow as the basis for determining insulin requirements.

Yet a further object of the present invention is to provide an insulin delivery system of the aforesaid type which may be miniaturized so as to be transportable and wearable by the user.

In accordance with the above and other objects, the present invention comprises a sensor which monitors, on a continuous basis, the blood flow in a selected portion of the digestive system. An electrical output provided by the sensor is conditioned and processed such that an appropriate does of insulin is computed and provided to the user. The monitoring is done on a continuous basis to allow the system to deliver insulin when needed in a manner which parallels that in the non-diabetic individual.

DISCLOSURE OF A PREFERRED EMBODIMENT

A fuller understanding of the present invention and the features and characteristics thereof will be made upon consideration of the following description of a preferred, but nonetheless illustrative, embodiment of the invention and the accompanying drawings, wherein.

Figure 10:
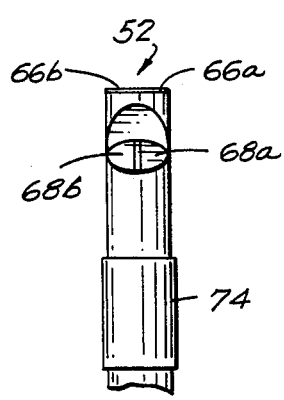

FIG. 10 a front elevation view of an alternative dual transducer sensor; and

Figure 11:
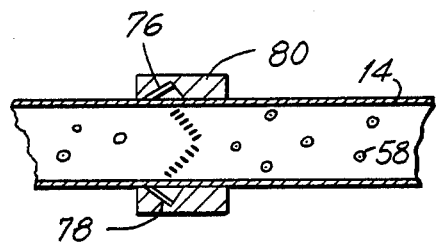

FIG. 11 is a diagrammatic representation of a cuff-type sensor in place on a blood vessel.

Figure 1:
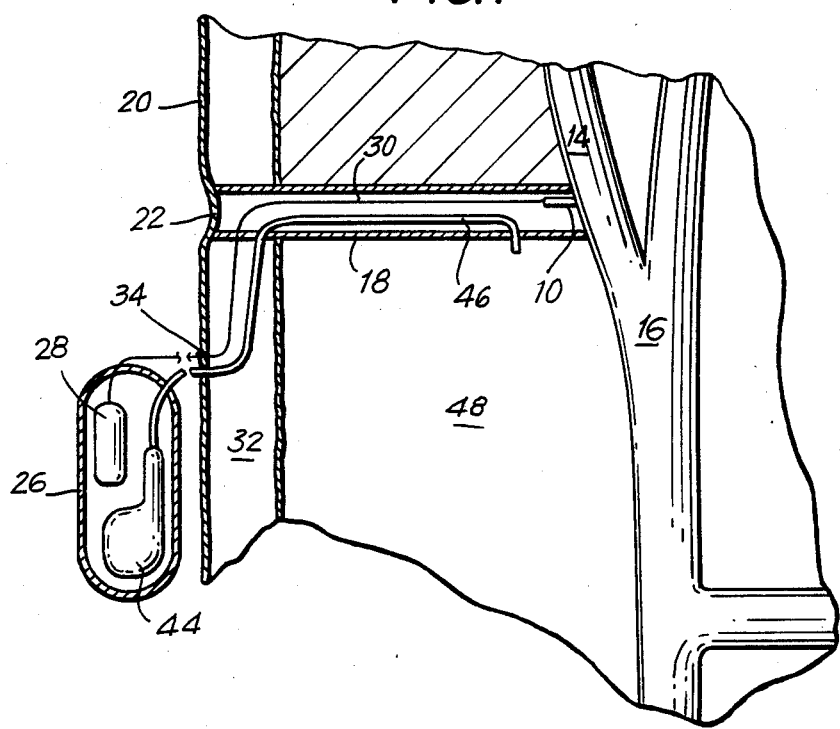
FIG. 1 is a diagrammatic representation of the present invention in place on the user.
Figure 2:
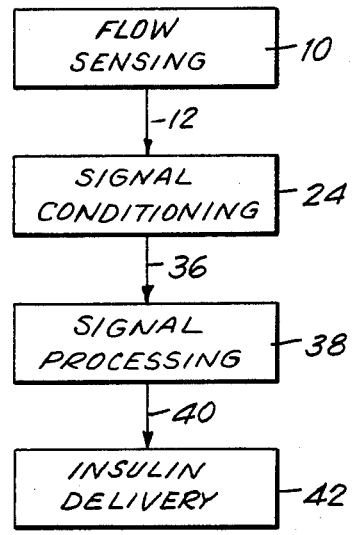
FIG. 2 is a block diagram setting forth the operative portions of the invention.

Referring to FIGS. 1 and 2, the present invention utilizes blood flow sensing means 10 to sense and provide an output signal 12 related to the flow of blood in the portion of the digestive tract at which the sensing means is located. The flow sensor 10 is advantageously located to monitor hepatic portal circulation and, in particular, flow in the left branch 14 of portal vein 16. Positioning of the sensor 10 proximate the portal vein is accomplished by introducing the sensor into the body via the obliterated umbilical vein 18, which terminates at the skin surface 20 at umbilicus 22.

The output signal 12 from sensor 10 is passed to signal conditioning means 24, which may include appropriate sensor energization circuitry as well as amplification and comparison circuitry necessary to produce a useable signal bearing the blood flow data. This signal conditioning circuitry may be located in an external pouch 26 which may be worn by the patient, and may comprise a portion of module 28 therein, which may also include signal processing means circuitry 38 as hereinafter described. The blood flow sensing means 10 is connected to signal conditioning circuitry 24 by wires 30, which may pass through a wall of the obliterated umbilical vein 18 into subcutaneous space 32 and exit the body through skin surface 20 by means of appropriate incisions at 34, as known in the art. Alternatively, pouch 26, or portions of its contents, may be implantable.

The output 36 of signal conditioning means 24 is passed to signal processing circuitry means 38, which may also be located in pouch 26 as a portion of module 28. Signal processing circuitry 38, which may be in the form of an appropriately programmed microcomputer, compares output signal 36 to a stored value which represents the mean or base line blood flow for the individual in the monitored portion of the circulatory system. To permit portability, both signal conditioning means 24 and signal processing means 38 may be battery powered.

When an upward deviation from this baseline value is present, signal processor 38 provides an output 40 to insulin delivery system 42, which may include an appropriate insulin reservoir and pump 44 located in pouch 26 and a delivery catheter 46 running from the pump and reservoir 44 through the skin surface 20 through an incision 34 into peritoneal cavity 48. Such reservoir/pump system may be in the form of a motor driven syringe or its equivalent. It is presently contemplated that with a sensed 15 percent increase in blood flow from the baseline level the delivery of 8 units of insulin per hour until baseline flow is again reached is an appropriate starting point for system operation.

Signal processing means 38 may include appropriate allow a record of blood flow and insulin delivery to be maintained so that fine tuning and adjustment of the system may be accomplished, either upon recovery and analysis of such data by appropriate personnel or on a real time basis by appropriate routines preprogrammed into system memory. With the use of such routines the sensing means 10 may be activated on periodic basis, with insulin needs being calculated based upon both instantaneous blood flow and past delivery history taken over an appropriate time interval. By adjusting the blood flow sampling rate the degree of fineness over the insulin delivery rate can be controlled as required. In some circumstances it may be necessary to provide essentially continuous analysis of blood flow for insulin delivery while in other cases blood flow sampling on an interval basis, such as hourly, may suffice. In either case the storage of past blood flow rate and insulin delivery data will allow determination of the appropriate delivery level.

Figure 3:
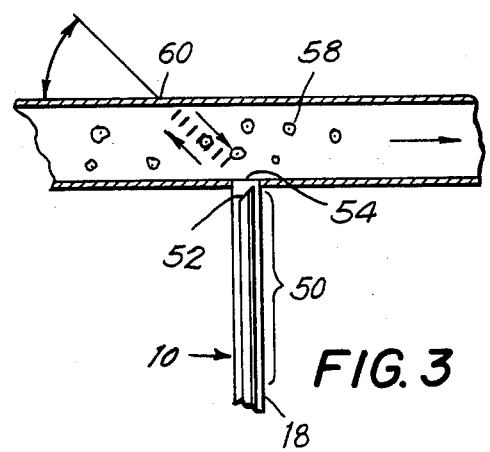
FIG. 3 is a diagrammatic representation of a blood flow sensor of the present invention positioned adjacent a blood vessel.
Figure 5:
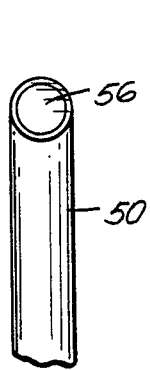
FIG. 5 is a front elevation view of the sensor of FIG. 3.
Figure 4:
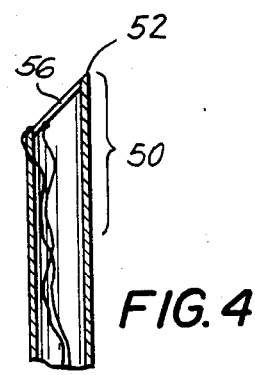
FIG. 4 is a more detailed side sectional elevation view of the sensor of FIG. 3.

As seen in FIGS. 3 through 11, sensor means 10 may take one of a variety of configurations. As depicted in FIGS. 3 through 5, the sensing means 10 may firstly comprise ultrasonic sensor device 50 positioned within the obliterated umbilical vein 18 such that its tip 52 is located proximate the portal vein/umbilical vein junction. in such a position it is separated from the portal vein 14 by only a thin connective tissue septum 54. Sensor 50 includes a piezoelectric transducer element 56 mounted at an angle to the sides of the sensor 50. Transducer 56 is energized on a pulse basis by appropriate circuitry in signal conditioning means 24 such that ultrasonic energy may be radiated and received at an angle. Backscattered energy from flowing blood cells 58 is subject to a Doppler shift proportional to the flow rate, so that blood velocity may be computed. In addition, reflected radiation from opposed vessel wall portion 60, not subject to Doppler shift, can be utilized to determine vessel cross-section. With these two values, flow velocity and vessel cross-section, total blood flow may be calculated.

Figure 6:
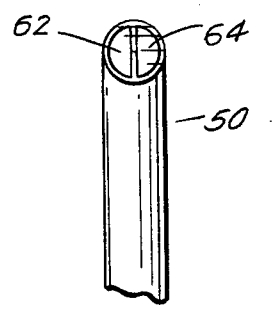
FIG. 6 is a front elevation view of an alternative embodiment for the blood flow sensor.
Figure 7:
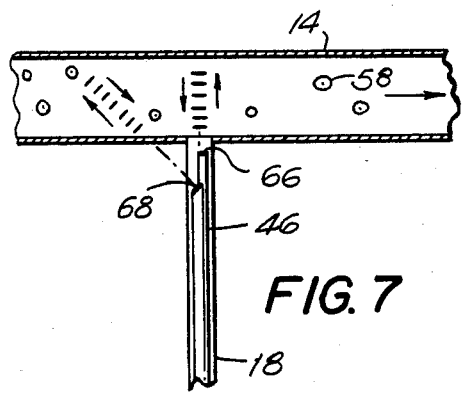
FIG. 7 is a diagrammatic representation of an alternative sensor utilizing dual transducer elements.

An alternative to the single transducer of FIGS. 4 and 5, in which the transducer serves both as a radiating and receiving element, is the dual transducer embodiment of FIG. 6. In this embodiment a first transducer 62 serves solely as a source of ultrasonic energy while transducer 64 serves as a receiver for the reflected signals. This allows energy to be emitted and received on a continuous basis.

In the embodiment of FIGS. 7 through 10 sensor 10 is provided with a first transducer means 66 positioned at a right angle to the wall of vein 18 and a second transducer means 68 at an angle thereto. In this embodiment transducer means 66 is utilized to provide information regarding vessel cross-section while transducer means 68 provides Doppler shift blood velocity data. The transducers 66, 68 may be mounted in an appropriate end block 70 of sensor means 10 with leads 72 being directed to the exterior of the body as previously described. Alternatively, transducer means 66 and 68 may each be comprised of a pair of transducers 66a, 66b and 68a, 68b, respectively, in which one element of each pair is utilized as the transmitter and the second as the receiver.

Figure 9:
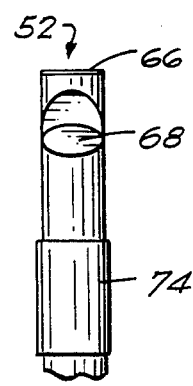
FIG. 9 is a front elevation view of the sensor of FIG. 8.
Figure 8:
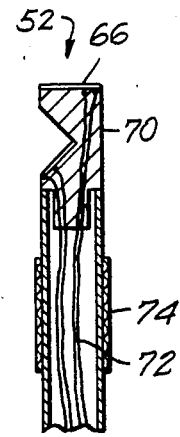
FIG. 8 is a side sectional elevation view of the sensor of FIG. 7.

As further illustrated in FIGS. 8 through 10, the sensor 10 can be provided with a collar 74 encircling the sensor proximate its operative tip 52. This collar may be formed of dacron or similar material which allows the surrounding tissue to grow into it. This tissue, which is generally of high collegen content, will then bind the catheter in position.

As depicted in FIG. 11, transducers 76, 78 may be located on cuff 80, which either completely or partially encircles vein 14 such that the transducers are located on opposite sides thereof. Either single or multiple transducers may be utilized, as known in the art, wherein the first transducer or group 76 transmits on a continuous basis and second transducer or group 78 serves as a receiver.

It is to be recognized by those skilled in the art that variations, adaptations and modifications to the invention as disclosed herein may be accomplished without departing from the intended scope thereof.

What is claimed is:

1. A method for providing for the insulin needs of a diabetic individual, comprising: mounting a blood flow sensor on the individual such that digestive tract blood flow may be monitored; monitoring said digestive tract blood flow and forming an electrical data signal relating thereto; computing the individual insulin needs based upon said electrical data signal; and delivering an amount of insulin responsive to said determined need to the individual.

2. The method of claim 1 wherein said step of monitoring blood flow comprises monitoring blood flow in the portal vein.

3. The method of claim 2 wherein said step of monitoring blood flow comprises the step of inserting a catheter containing monitoring means proximate said portal vein through the obliterated umbilical vein.

4. The method of claim 1 wherein said processing step comprises comparing sensed blood flow rate to a predetermined level and said delivery step comprises delivering insulin at a pre-established rate until said blood flow rate returns to said pre-determined level.

5. A method for providing of the insulin needs of an individual, comprising: mounting a blood flow sensor on the individual such that digestive tract blood flow may be monitored; monitoring said digestive tract blood flow and forming a data signal embodying such blood flow data at a first time; computing the individual's insulin needs based upon said blood flow data; delivering an amount of insulin responsive to said computed insulin need; storing said blood flow and insulin amount in memory means; sampling said digestive tract blood flow at a second time; recalculating said individual's insulin needs based upon said second time blood flow data and said stored blood flow and insulin amount data; and storing said recalculated insulin amount and second time blood flow data in system memory.

6. Apparatus for administering insulin to a patient in accordance with the patient's requirements, comprising a blood flow sensor located upon the patient to sense digestive tract blood flow; control means operatively connected to said flow sensor to calculate the insulin need of the patient based upon data received from said flow sensor; and insulin dispensing means operatively connected to said control means to administer the amount of insulin calculated by said control means.

7. The apparatus of claim 6 wherein said blood flow sensor comprises ultrasonic transducer means.

8. The apparatus of claim 7 wherein said ultrasonic transducer means comprises a catheter positioned to monitor blood flow in the digestive system.

9. The apparatus of claim 8 wherein said catheter is located approximate the portal vein.

10. The apparatus of claim 9 wherein said catheter is located within the obliterated umbilical vein.

11. The apparatus of claim 10 wherein said control means comprises a microprocessor.

12. The apparatus of claim 11 wherein said control means includes means for periodic storage of blood flow data received from said blood flow sensor and administered insulin data.

13. The apparatus of claim 12 wherein said control means calculates the insulin need of the patient based upon the data received from said flow sensor and said stored blood flow and administered insulin data.

14. The apparatus of claim 11 wherein said control means is mounted in a pouch worn by the user.

15. The apparatus of claim 13 wherein said control means is operatively connected to said blood flow sensor by electrical signal transmission means located at least partially within the obliterated umbilical vein.

16. The apparatus of claim 11 when said control means is battery powered.

* * * * *